United States Patent
Chen et al.

(10) Patent No.: US 10,246,412 B2
(45) Date of Patent: Apr. 2, 2019

(54) CHEMICAL FILM ON SUBSTRATE AND METHOD OF FORMING THE SAME, METHOD OF FORMING PARACYCLOPHANE CONTAINING FUNCTIONAL GROUND WITH DISULFIDE BOND

(71) Applicant: MAY-HWA ENTERPRISE CORPORATION, Taipei (TW)

(72) Inventors: Hsien-Yeh Chen, Taipei (TW); Zhen-Yu Guan, Taipei (TW); Chih-Yu Wu, Taipei (TW)

(73) Assignee: MAY-HWA ENTERPRISE CORPORATION, Taipei (TW)

( * ) Notice: Subject to any disclaimer, the term of this patent is extended or adjusted under 35 U.S.C. 154(b) by 145 days.

(21) Appl. No.: 15/185,003

(22) Filed: Jun. 16, 2016

(65) Prior Publication Data

US 2017/0166520 A1    Jun. 15, 2017

(30) Foreign Application Priority Data

Dec. 10, 2015    (TW) .............................. 104141604 A (51) Int. Cl.
| | | |
|---|---|---|
| *C07C 319/22* | (2006.01) | |
| *C07C 17/16* | (2006.01) | |
| *C07C 29/14* | (2006.01) | |
| *C07C 45/30* | (2006.01) | |
| *C07C 209/08* | (2006.01) | |

(Continued)

(52) U.S. Cl.
CPC ............ *C07C 319/22* (2013.01); *C07C 17/16* (2013.01); *C07C 22/04* (2013.01); *C07C 29/14* (2013.01); *C07C 45/30* (2013.01); *C07C 45/45* (2013.01); *C07C 209/08* (2013.01); *C09D 165/04* (2013.01); *C07C 2603/92* (2017.05); *C08G 2261/145* (2013.01); *C08G 2261/1426* (2013.01); *C08G 2261/1432* (2013.01); *C08G 2261/3424* (2013.01)

(58) Field of Classification Search
CPC ....... C07C 319/22; C07C 17/16; C07C 29/14; C07C 45/30; C07C 45/45; B01J 37/0238
See application file for complete search history.

(56) References Cited

U.S. PATENT DOCUMENTS

2007/0272122 A1* 11/2007 Lahann .................. B01J 20/285
106/285

FOREIGN PATENT DOCUMENTS

| TW | 201428020 A | 7/2014 |
| TW | 201527279 A | 7/2015 |

OTHER PUBLICATIONS

Hans-George Elias, "Specialty Plastics," Ullmann's Encyclopedia of Industrial Chemistry, vol. 34, 17-38, published online 2000.*

(Continued)

*Primary Examiner* — Nicholas E Hill
(74) *Attorney, Agent, or Firm* — Burris Law, PLLC (57) ABSTRACT

The present invention provides a method of forming paracyclyophane containing disulfide functional group. The paracyclophane is prepared by adding 3,3'-dithiodipropionic acid (DPDPA) and N-ethyl-N'-(3-(dimethylamino)propyl) carbodiimide (EDC) into 4-aminomethyl [2,2] paracyclophane. The present invention further provides a chemical film and a method of forming the same. The chemical film contains poly-p-xylylene with disulfide functional group and is formed on a substrate by a chemical vapor deposition process.

5 Claims, 9 Drawing Sheets

Specification includes a Sequence Listing.

(51) Int. Cl.
*C09D 165/04* (2006.01)
*C07C 45/45* (2006.01)
*C07C 22/04* (2006.01)

(56) References Cited

OTHER PUBLICATIONS

Guan et al., "Switching the Biointerface of Displaceable Poly-p-xylylene Coatings", ACS Appl. Mater. Interfaces 2015, 7, pp. 14431-14438. doi: 10.1021/acsami.5b03286, Jun. 17, 2015.

Wu et al., "Customizable Optical and Biofunctional Properties of a Medical Lens Based on Chemical Vapor Deposition Encapsulation of Liquids", Chemistry of Materials, Sep. 28, 2015, 27(20), pp. 7028-7033.

Ross et al., Selective and Reversible Binding of Thiol-Functionalized Biomolecules on Polymers Prepared via Chemical Vapor Deposition Polymerization, Langmuir, Apr. 14, 2015, 31, pp. 5123-5129.

* cited by examiner

SEQUENCE LISTING

<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<221> NAME/KEY: FITC-conjugated peptide
<223> OTHER INFORMATION: the sequence is synthesized in the laboratory

```
<400> SEQUENCE: 1

Arg Arg Arg Gly Asp
1               5

<210> SEQ ID NO 2
<211> LENGTH: 6
<212> TYPE: PRT
<213> ORGANISM: Artificial Sequence
<220> FEATURE:
<221> NAME/KEY: hydrophilic component
<223> OTHER INFORMATION: the sequence is synthesized in the laboratory

<400> SEQUENCE: 2

Cys Lys Asp Lys Asp Asp
1               5

<210> SEQ ID NO 3
<211> LENGTH: 6
<212> TYPE: PRT
<213> ORGANISM: Artificial Sequence
<220> FEATURE:
<221> NAME/KEY: Paralene S-S coated peptide
<223> OTHER INFORMATION: the sequence is synthesized in the laboratory

<400> SEQUENCE: 3

Arg Gly Asp Tyr Tyr Cys
1               5
```

CHEMICAL FILM ON SUBSTRATE AND METHOD OF FORMING THE SAME, METHOD OF FORMING PARACYCLOPHANE CONTAINING FUNCTIONAL GROUND WITH DISULFIDE BOND

BACKGROUND OF THE INVENTION

1. Field of the Invention

The present invention is related to a chemical film, a method of forming the same and more particularly, to a paracyclophane film containing functional group with disulfide bond.

2. Description of the Prior Art

Reactions and interactions which occur on a surface of a material, as well as the structure and composition of the material as observed from the surface, are greatly different from what can be seen from a macroscopic view. Although those in the field have studied responses to various materials for many years, especially in the field of biomedical interface science, interface science is still considered revolutionary. In the last half century, rapid development of equipment facilitated the development of interface science, material science, and bioscience, which has enabled people in the field to analyze surface compositions of bio-molecular structures. Accordingly, the current status of interface science is well set to study physical and chemical phenomena that occur at the surface or interface of two phases and two cells. Recent reports have demonstrated that surface characteristics are significantly related to biological performances such as protein bond and cytogenesis.

In conventional arts, chemical vapor deposition (CVD) is regarded as one of the best synthesizing systems to prepare poly-para-xylylenes. Prepared poly-para-xylylenes have the characteristics of biocompatibility, biostability, moisture-proofing, chemical resistance, and dielectric property. Conventional poly-p-xylylene coated film does not have any anchor compound which can receive other molecules for additional modification, however, and is poor when used as a connection compound for other biomolecules. Although plenty of methods have been developed to prepare functional compounds that can be used as an anchor compound in the modification process, as well as further modifying the poly-p-xylylene coated film, it is still limited in practical use. For example, disulfide bond is regarded as a significant functional compound in biomaterials science, due to its capability of connecting other molecules through a thiol-disulfide interchange reaction, so as to change the biointerface functions.

However, there are still no appropriate method for forming a paracyclophane film containing functional group with disulfide bond and no appropriate CVD method to form a paracyclophane film on a substrate.

SUMMARY OF THE INVENTION

The present invention therefore provides a chemical film, a method of forming the chemical film, and a paracyclophane film containing functional group with disulfide bond, thereto meet the above requirements.

According to one embodiment, the present invention provides a method of forming paracyclyophane containing disulfide functional group. The paracyclophane is prepared by adding 3,3'-dithiodipropionic acid (DPDPA) and N-ethyl-N'-(3-(dimethylamino)propyl)carbodiimide (EDC) into 4-aminomethyl [2,2] paracyclophane. The present invention further provides a chemical film and a method of forming the same. The chemical film contains poly-p-xylylene with disulfide functional group and is formed on a substrate by a chemical vapor deposition process.

These and other objectives of the present invention will no doubt become obvious to those of ordinary skill in the art after reading the following detailed description of the preferred embodiment that is illustrated in the various figures and drawings.

DETAILED DESCRIPTION

To provide a better understanding of the present invention, preferred embodiments are detailed as follows. The preferred embodiments are also illustrated in the accompanying drawings to clarify the contents and effects of the present invention.

Figure 1:
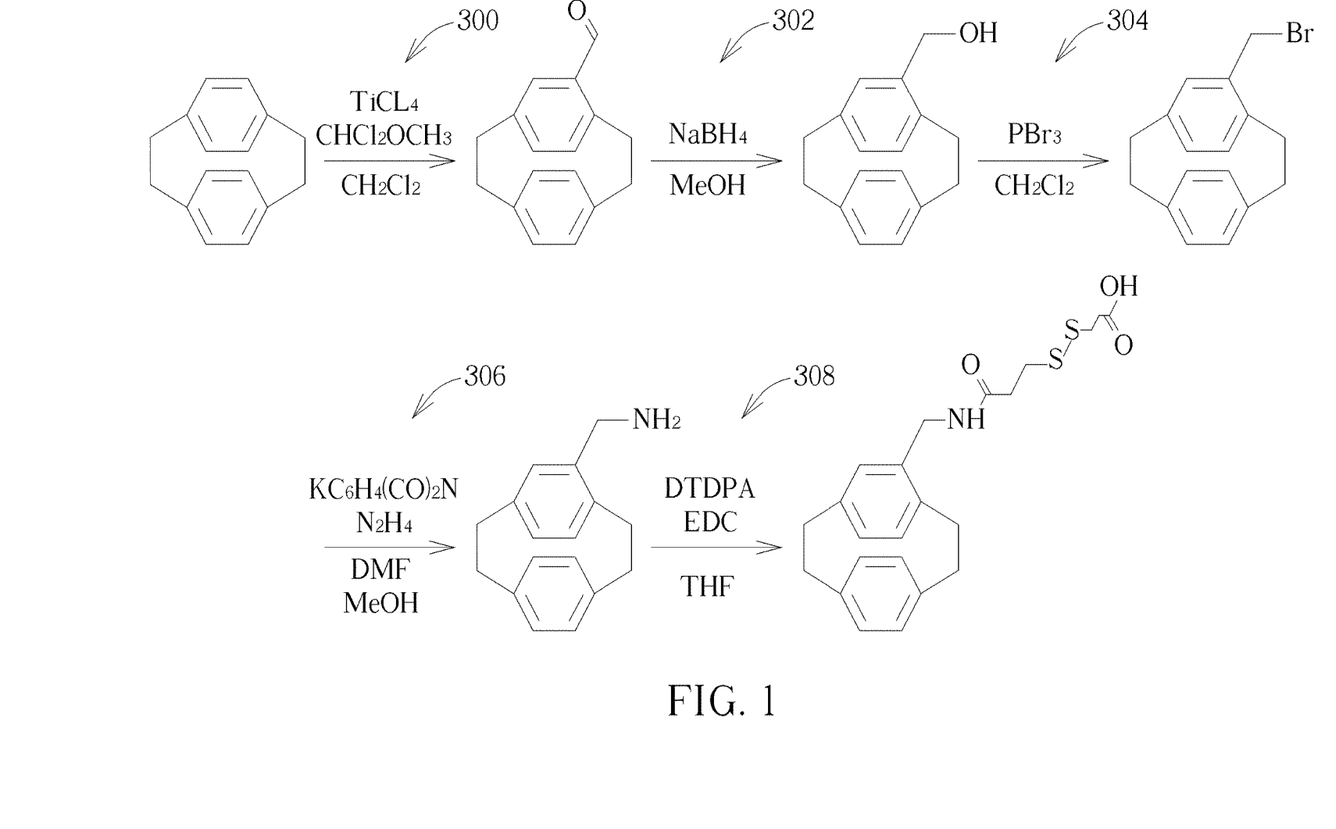
FIG. 1 shows a schematic diagram of the method for forming paracyclophane containing disulfide functional group according to one embodiment of the present invention.

Please refer to FIG. 1, which shows a schematic diagram of the method for forming paracyclophane containing disulfide functional group according to one embodiment of the present invention. As shown in FIG. 1, the method provided in the present invention includes:

Step 300: Adding paracyclophane into a, a-dichloromethyl methyl ether ($CHCl_2OCH_3$), thereby obtaining 4-formyl [2,2] paracyclophane. In one embodiment, the step further includes adding titanium chloride, e.g., titanium tetrachloride ($TiCl_4$) as a catalyst. In another embodiment, the paracyclophane is dissolved into anhydrous dichloromethane ($CH_2Cl_2$).

Step 302: Performing a reduction reaction to convert 4-formyl [2,2] paracyclophane to 4-hydroxymethyl [2,2] paracyclophane. In one embodiment, the reductant of the reaction is sodium borohydride ($NaBH_4$). In one embodiment, the 4-formyl [2,2] paracyclophane is dissolved in methanol (MeOH).

Step 304: Adding phosphorus tribromide ($PBr_3$) into 4-hydroxymethyl [2,2] paracyclophane, to form 4-bromomethyl [2,2] paracyclophane. In one embodiment, 4-hydroxymethyl [2,2] paracyclophane is dissolved in anhydrous dichloromethane ($CH_2Cl_2$).

Step 306: Adding potassium phthalimide ($KC_6H_4(CO)_2N$) and hydrazine ($N_2H_4$) into 4-bromomethyl [2,2] paracyclophane to form 4-aminomethyl [2,2] paracyclophane. In one embodiment, 4-bromomethyl [2,2] paracyclophane is first dissolved in dimethylformamide (DMF) and then added with potassium phthalimide. After the organic phase is extracted, it is then dissolved in methanol and added with hydrazine ($N_2H_4$).

Step 308: Adding 3,3'-dithiodipropionic acid (DPDPA) and (N-ethyl-N'-(3-(dimethylamino)propyl)carbodiimide (EDC) into 4-aminomethyl [2,2] paracyclophane, to obtain 4-(3-((3-methylamido)-disulfide) propanoic acid) [2,2] paracyclophane. In one embodiment, the 4-aminomethyl [2,2] paracyclophane is dissolved in tetrahydrofuran (($CH_2)_4O$, THF).

Through the above steps, a paracylophane film containing functional group with disulfide bond, such as a paracylophane with thiol-disulfide carboxylic acid end group is therefore be obtained. In the following paragraphs, each step of the method will be further detailed using (4-(3-((3-methylamido)-disulfide)propanoic acid) [2,2] paracyclophane as an example. It is noted that the chemical manufacturing company described below is only one example in the present invention and is not to the limitation to the scope the claimed invention.

Five steps are shown in the below contexts, which are corresponding to the step 300 to step 308 in FIG. 1. 4-(3-((3-Methylamido)disulfide)propanoic acid) [2,2] paracyclophane was synthesized via a five-step procedure from commercially available [2,2] paracyclophane (Sigma-Aldrich, St. Louis, Mo., USA). Titanium (IV) chloride (8.4 mL, 77 mmol) (Sigma-Aldrich) was added slowly to an ice-cooled solution of [2,2]paracyclophane (8.0 g, 38 mmol) in anhydrous $CH_2Cl_2$ (400 mL) under a nitrogen environment. The mixture was stirred for 20 min, followed by the dropwise addition of α,α-dichloromethyl methyl ether (4.0 mL, 44 mmol; Sigma-Aldrich). The reaction mixture was stirred at room temperature for 6 h, subsequently poured into water, and then stirred for an additional 2 h (200 mL). Next, the organic layer was washed with 3 M HCl (2×300 mL) and then with water (2×300 mL), after which it was dried over $MgSO_4$. After filtration and removal of the solvent, the crude product was purified on silica gel using hexane/C $H_2Cl_2$ (5/1) as the eluent to yield 4-formyl [2,2] paracyclophane as white crystals (6.6 g, 83%).

The crystals were then dissolved in a mixture of MeOH (200 mL) and anhydrous tetrahydrofuran (THF; 10 mL). $NaBH_4$ (2.1 g, 28 mmol; Sigma-Aldrich) was added carefully to this solution, and the mixture was stirred at room temperature for 3 h. The excess $NaBH_4$ was then decomposed by the careful addition of water. The solution was then diluted with EtOAc (200 mL), washed with 3 M HCl (3×200 mL) and then with water (2×200 mL), and dried over MgSO4. After filtration and removal of the solvent, 4-hydroxymethyl [2,2] paracyclophane was obtained as white crystals (6.0 g, 75%), which were used without further purification. The 4-hydroxymethyl [2,2] paracyclophane was dissolved in anhydrous $CH_2Cl_2$ (200 mL) and cooled to 0° C. under a nitrogen environment.

Next, $PBr_3$ (3.00 mL, 31.8 mmol; Sigma-Aldrich) was added dropwise, and the mixture was stirred for 4 h. The reaction was hydrolyzed by the addition of water (150 mL), and the phases were separated. The organic layer was washed with 1 M HCl (150 mL), saturated $NaHCO_3$ solution (150 mL), and saturated NaCl solution (150 mL). It was then dried over $MgSO_4$ and filtered, after which the solvent was removed in vacuum. The crude product 4-bromomethyl [2,2] paracyclophane (5.81 g, 77%) was used in the next step without further purification.

Crude 4-bromomethyl [2,2] paracyclophane and potassium phthalimide (3.71 g, 20.0 mmol; Sigma-Aldrich) were dissolved in dimethylformamide (100 mL) and heated to 80° C. for 4 h. After complete conversion (TLC control), the solvent was removed in vacuum and the residue was dissolved in EtOAc (500 mL) and washed with saturated NaCl solution (400 mL). The aqueous phase was extracted with $CH_2Cl_2$ (2×200 mL), and the combined organic phases were dried over MgSO4. After removal of the solvent, the crude product (7.06 g) was dissolved in MeOH (300 mL) and hydrazine (19 mL, 80% in water; Sigma Aldrich) was added. The reaction mixture was heated to 60° C. for 1 h (TLC control). Next, the solvent was removed, and the residue was taken up in $CH_2Cl_2$ (500 mL) and 1 M NaOH solution (300 mL). The phases were separated, and the aqueous phase was extracted with $CH_2Cl_2$ (300 mL). The combined organic phases were washed with 1 M. NaOH (300 mL) and brine (300 mL). The organic phase was dried over MgSO4, and the solvent was removed in vacuo. The crude product was purified on silica gel using $CH_2Cl_2$/MeOH (9/1) to yield 4-aminomethyl[2,2]paracyclophane (2.57 g, 56%).

Next, 3,3'-dithiodipropionic acid (2.10 g, 10 mmol; Sigma-Aldrich) and Nethyl-N'-(3-(dimethylamino)propyl)carbodiimide (EDC; 1.55 g, 10 mmol; Alfa Aesar, Ward Hill, Md., USA) were dissolved in anhydrous THF (250 mL) and stirred at room temperature for 20 min. 4-Aminomethyl [2,2]paracyclophane (2.37 g) was added to the resulting solution and reacted at room temperature for 12 h. The reaction product was washed with saturated $NaHCO_3$ solution (3×500 mL) and dried over $MgSO_4$. The crude product was purified on silica gel using hexane/ethyl acetate (5/1) to yield 4-(3-((3-methylamido)-disulfide)propanoic acid) [2,2] paracyclophane as white crystals (2.71 g, 63%).

Figure 2:
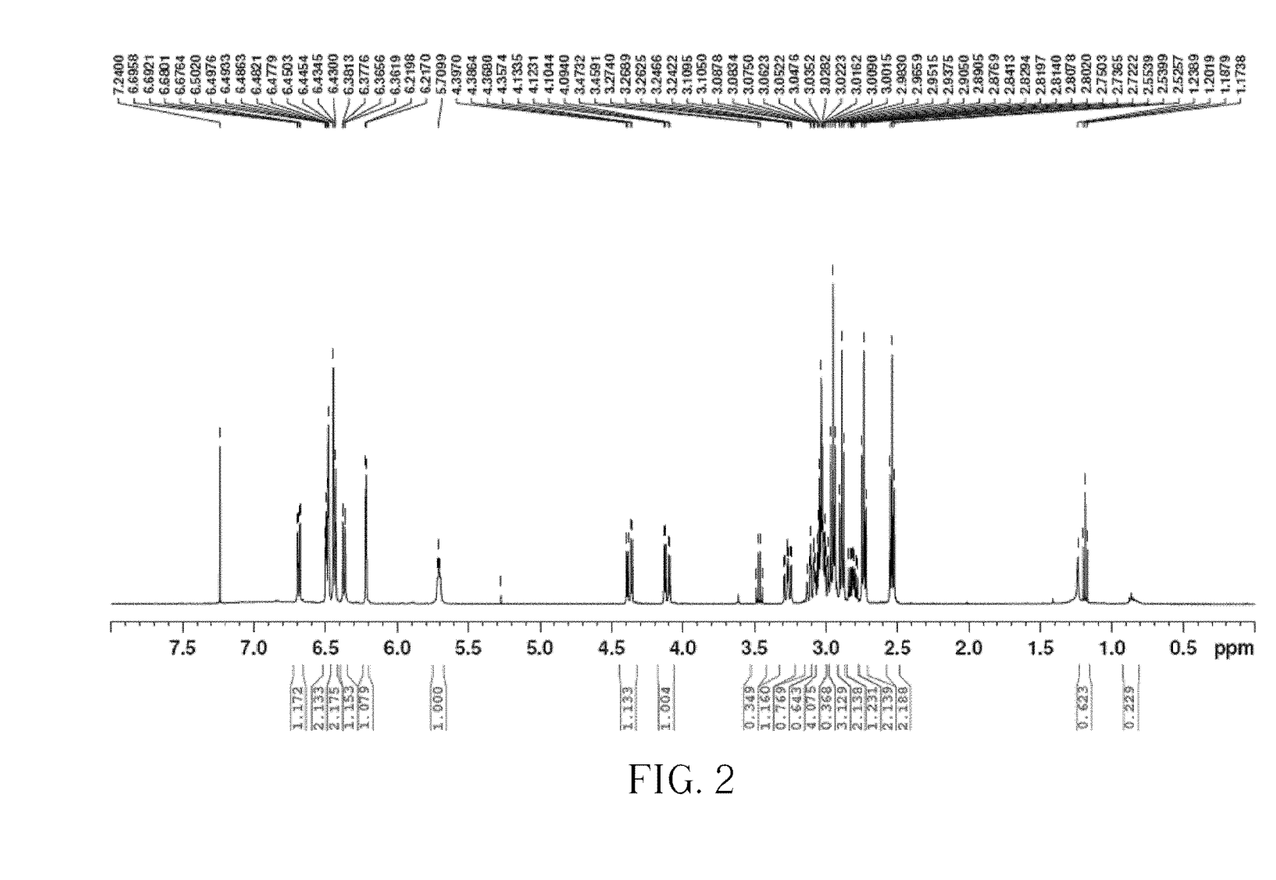
FIG. 2 is a $^1$H NMR spectrum of 4-(3-((3-methylamido)-disulfide)propanoic acid) [2,2]paracyclophane.
Figure 3:
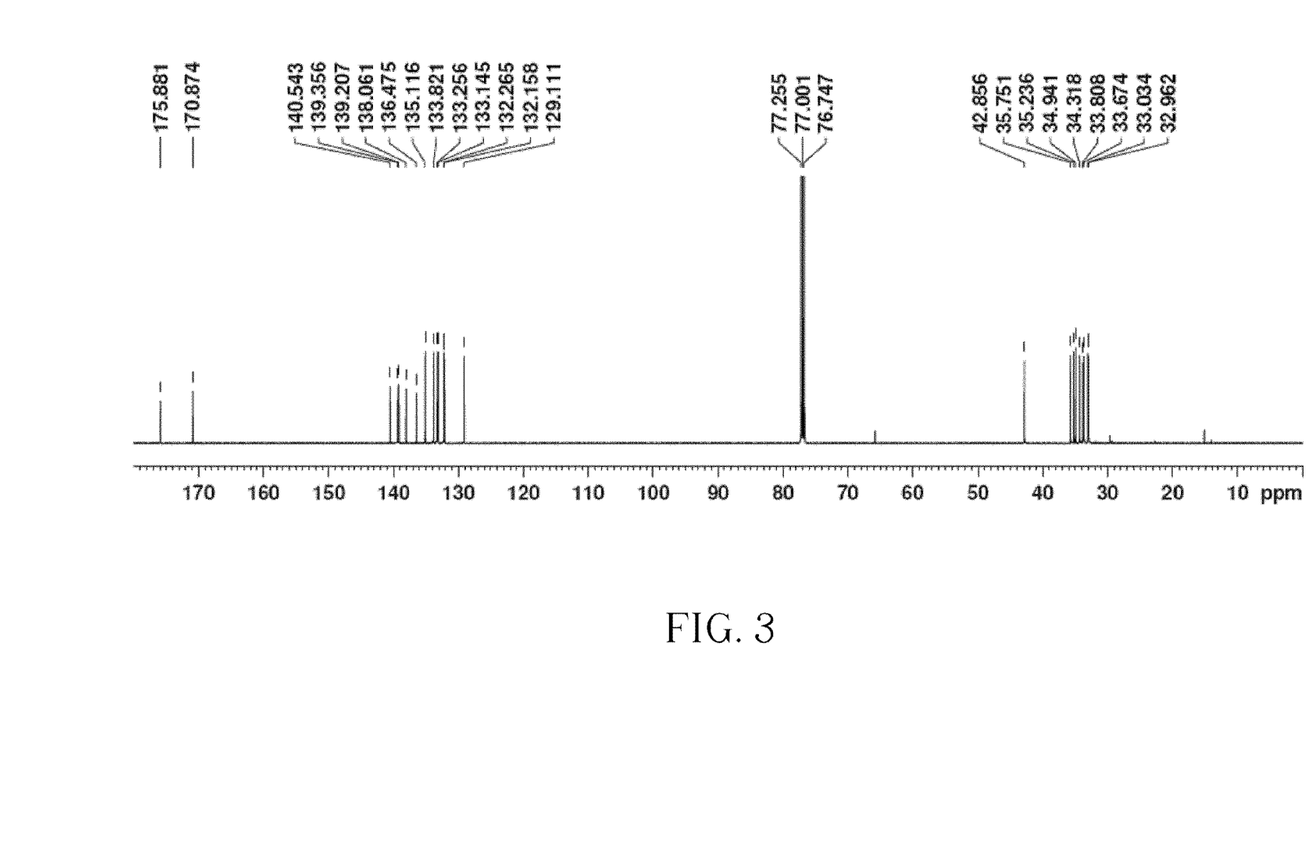
FIG. 3 is a $^{13}$C NMR spectrum of 4-(3-((3-methylamido)-disulfide)propanoic acid) [2,2]paracyclophane.
Figure 4:
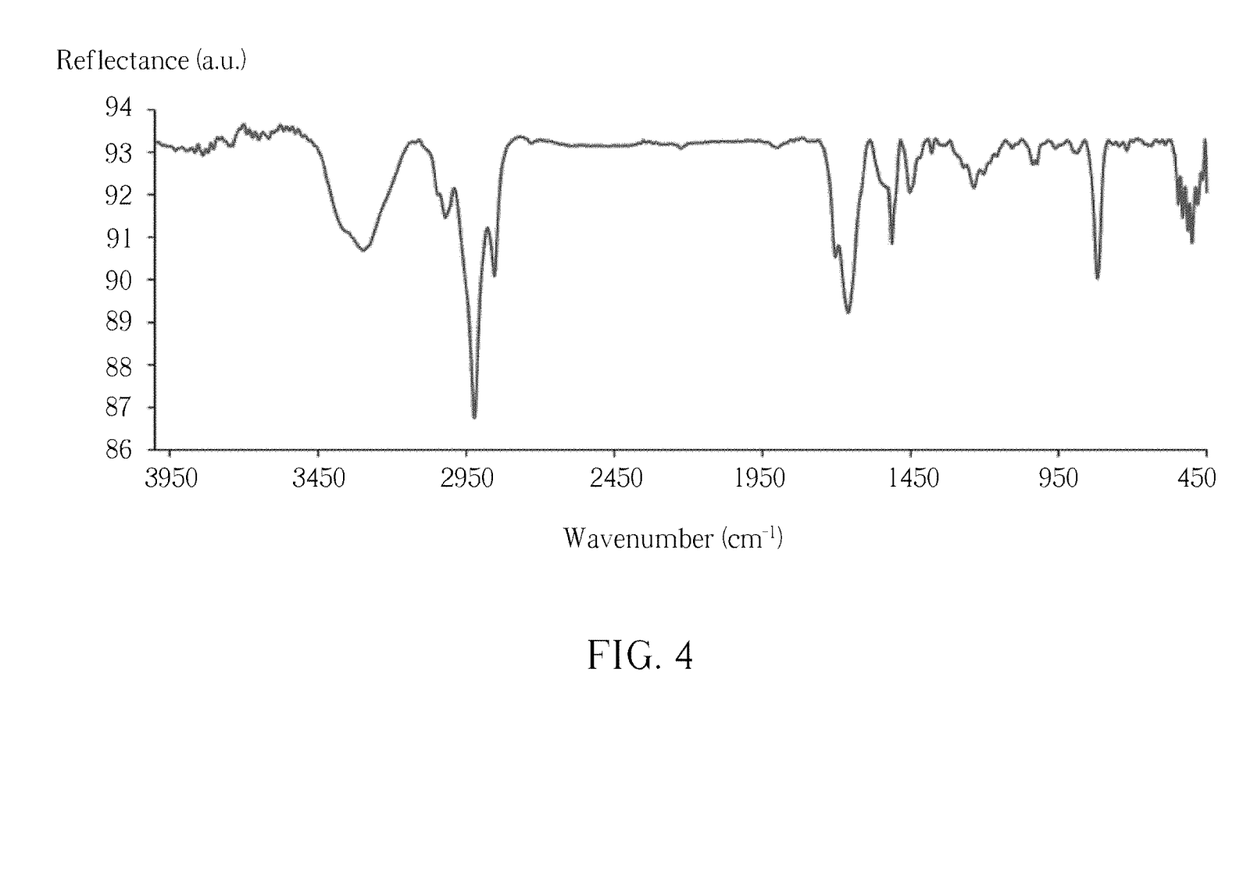
FIG. 4 is a FT-IR spectrum of 4-(3-((3-methylamido)-disulfide)propanoic acid) [2,2]paracyclophane.
Figure 5:
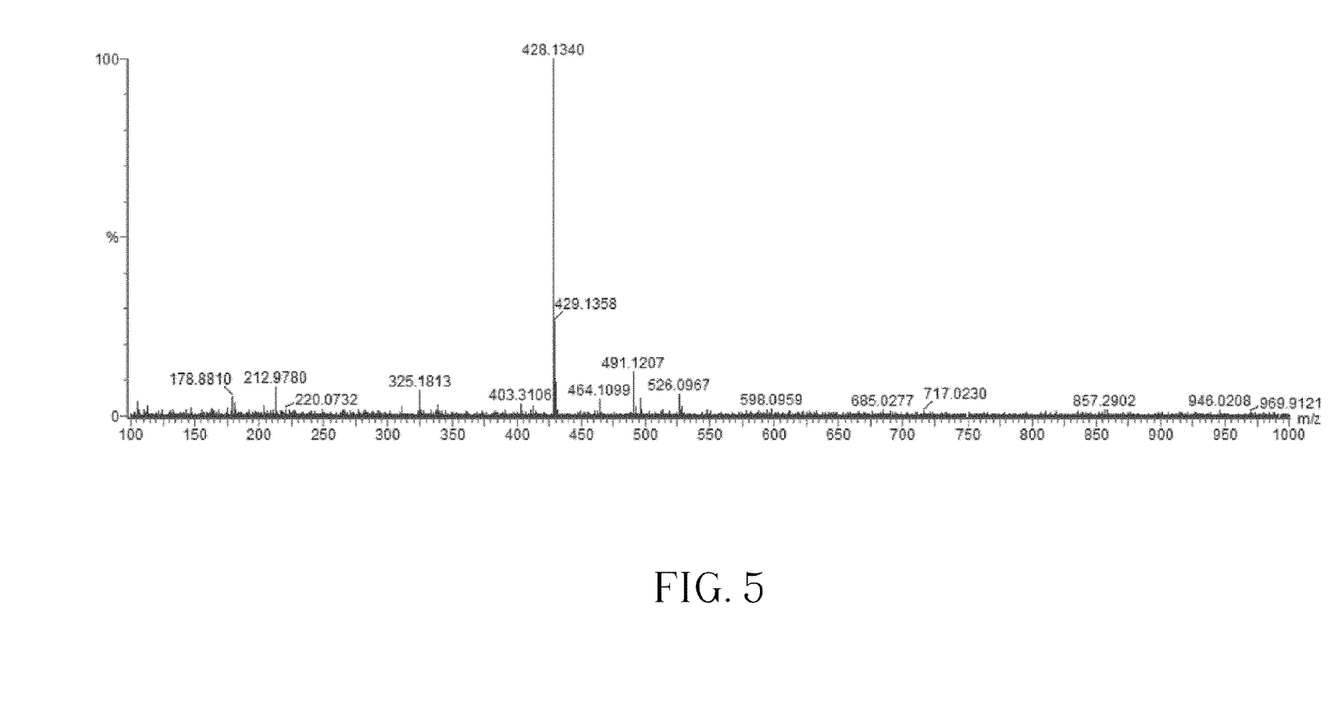
FIG. 5 is a ESI-MS spectrum of 4-(3-((3-methylamido)-disulfide)propanoic acid) [2,2]paracyclophane.

The following parameters were obtained from NMR, FT-IR, and ESI-MS analyses of the product. Please refer to FIG. 2, FIG. 3, FIG. 4 and FIG. 5. FIG. 2 is a $^1H$ NMR spectrum, FIG. 3 is a $^{13}C$ NMR spectrum FIG. 4 is a FT-IR spectrum, and FIG. 5 is a ESI-MS spectrum of 4-(3-((3-methylamido)-disulfide)propanoic acid) [2,2]paracyclophane. As shown in FIG. 2, the parameters of 1H NMR: (500 MHz, CDCl3, TMS): δ 6.67-6.69 (2d, J=1.9Hz, 1.9Hz, 1H), 6.36-6.50 (m, 5H), 6.21 (d, J=1.40 Hz, 1H), 5.71 (s, 1H), 4.35-4.40 (2d, J=5.3 Hz, 5.3 Hz, 1H), 4.09-4.13 (2d, J=5.2 Hz, 5.2 Hz, 1H), 2.72-3.47 (m, 16H), 2.52-2.55 (t, J=14.1 Hz, 2H). As shown in FIG. 3, the parameters of $^{13}C$ NMR (125 MHz, CDCl3, TMS): δ 32.9, 33.0, 33.6, 33.8, 34.3, 34.9, 35.2, 35.7, 42.8, 129.1, 132.1, 132.2, 133.1, 133.2, 133.8, 135.1, 136.4, 138.0, 139.2, 139.3, 140.5, 170.8, 175.8. As shown in FIG. 4, the parameters of FT-IR:3291 (m), 3024 (w), 2924 (m), 2853 (w), 1704 (s), 1668 (s), 1621 (m), 1520 (w), 1513 (m), 1444 (m), 1419 (m), 1332 (w), 1231 (w), 1204 (w), 1181 (w), 1041 (m), 940 (vw), 890 (vw), 823 (m), 762 (vw), 725 (vw), 624 (vw), 548 (w), 519 (m), 492 (w). As shown in FIG. 5, the parameters of ESI-MS: m/z (%) 428.15 (100) [M+]. With such spectra datum, it is demonstrated that the method of according to the present invention can obtain 4-(3-((3-methylamido)-disulfide)propanoic acid) [2,2]paracyclophane as products.

As shown in reaction (1) illustrated below, the obtained paracyclophane containing disulfide functional group can be further polymerized through a pyrolysis process, and then coated on a substrate through a chemical vapor deposition (CVD) process to form a chemical film comprising N-hydroxysuccinimide ester-functionalized poly-p-xylylene. In one preferred embodiment, R is a functional group containing disulfide bond, such as a functional group containing thiol-disulfide carboxylic acid end group, and in one preferred embodiment, R is 4-(3-((3-methylamido)-disulfide) propanoic acid.

Figure 6:
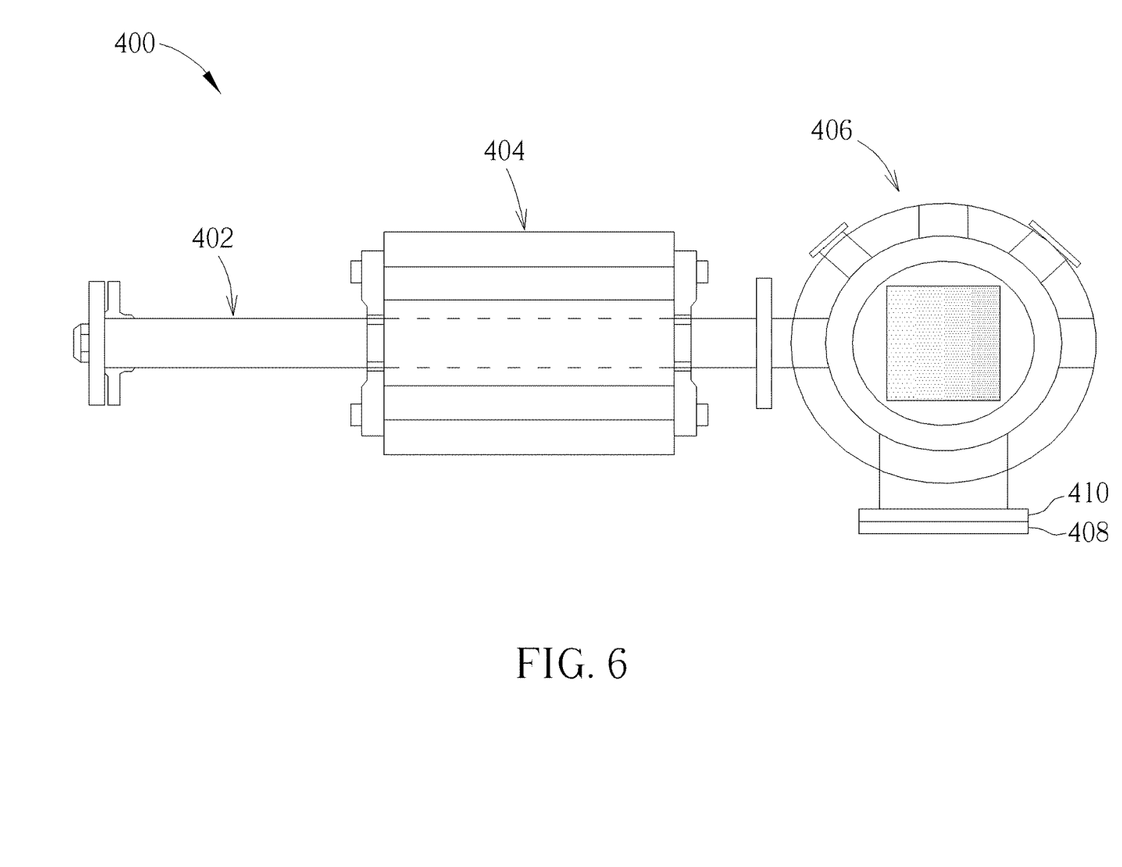
FIG. 6 is a diagram illustrating a chemical vapor deposition system used in the present invention.

FIG. 6 is a diagram illustrating a chemical vapor deposition system used in the present invention. As shown in FIG. 6, the chemical vapor deposition system 400 comprises a sub lamination zone 402, a pyrolysis zone 404, and a deposition chamber 406. The paracyclophane containing disulfide functional group is inhaled from the sub lamination zone 402, undergoes a pyrolysis process in the pyrolysis zone 404, and is then deposited on a substrate 408 placed on the deposition chamber 406. In this way, a chemical film 410 comprising the poly-p-xylylene containing disulfide functional group is obtained.

In one embodiment, parylene S—S coating was synthesized using a CVD polymerization process starting from the dimeric 4-(3-((3-methylamido)disulfide)propanoic acid) [2,2]paracyclophane. The dimer was first sublimated in the sublimation zone at approximately 125° C. The sublimated species was then transferred in a stream of argon carrier gas at a flow rate of 30 cm$^3$ (STP) min$^{-1}$ to the pyrolysis zone, in which the temperature was controlled at 550° C. Following pyrolysis, the radicals were transferred into the deposition chamber and then polymerized onto substrate materials on a rotating holder at 25° C. to ensure a uniform deposition of the Parylene S—S coating. The chamber wall was held at 90° C. to prevent any residual deposition. A pressure of 75 mTorr was maintained throughout the CVD polymerization process, and all deposition rates were regulated at approximately 0.5 ø/s, monitored on the basis of in situ quartz crystal micro balancing analysis (STM-100/MF, Sycon Instruments, East Styracuse, N.Y., USA). The as-deposited parylene S—S coating was mechanically stable under a cross-cut tape adhesion test, as well as a thermostability test carried out at 150° C.

In one embodiment of the present invention, the substrate 408 can be any material capable of being used in the chemical vapor deposition process, such as a semiconductor, ceramics, glass, metal or any composition thereof. The semiconductor can be silicon or germanium. The glass can optionally be any doped glass or undoped glass. The metal can be copper (Cu), silver (Ag) or titanium (Ti), and can also be alloy, such as titanium alloy (Ti$_6$Al$_4$V). The composition can be any resin polymer, such as polystyrene (PS), or polymethylmethacrylate (PMMA). The substrate 408 can be a combination of the aforementioned materials, such as a silicon substrate having a silver film, but is not limited thereto. In another embodiment of the present invention, the substrate 408 can be a biological duct, stent, or pacemaker, but is not limited thereto.

The switching and/or displacing ability of Parylene S—S coating was first achieved by dynamically altering its surface chemical composition. The attached functional molecule is detached from the surface under reduction conditions, and a new surface function is subsequently assembled by the disulfide interchange reaction to attach the second functional molecule. In this way, the biological function of the surface is correspondingly altered from one function to another. In one embodiment, biomolecules including 6-amine-1-hexanethiol and thiol terminated biotin (thiol-PEG-biotin) were used as examples, and their exchange was performed on identical samples of Parylene S—S coated substrates.

Figure 7:
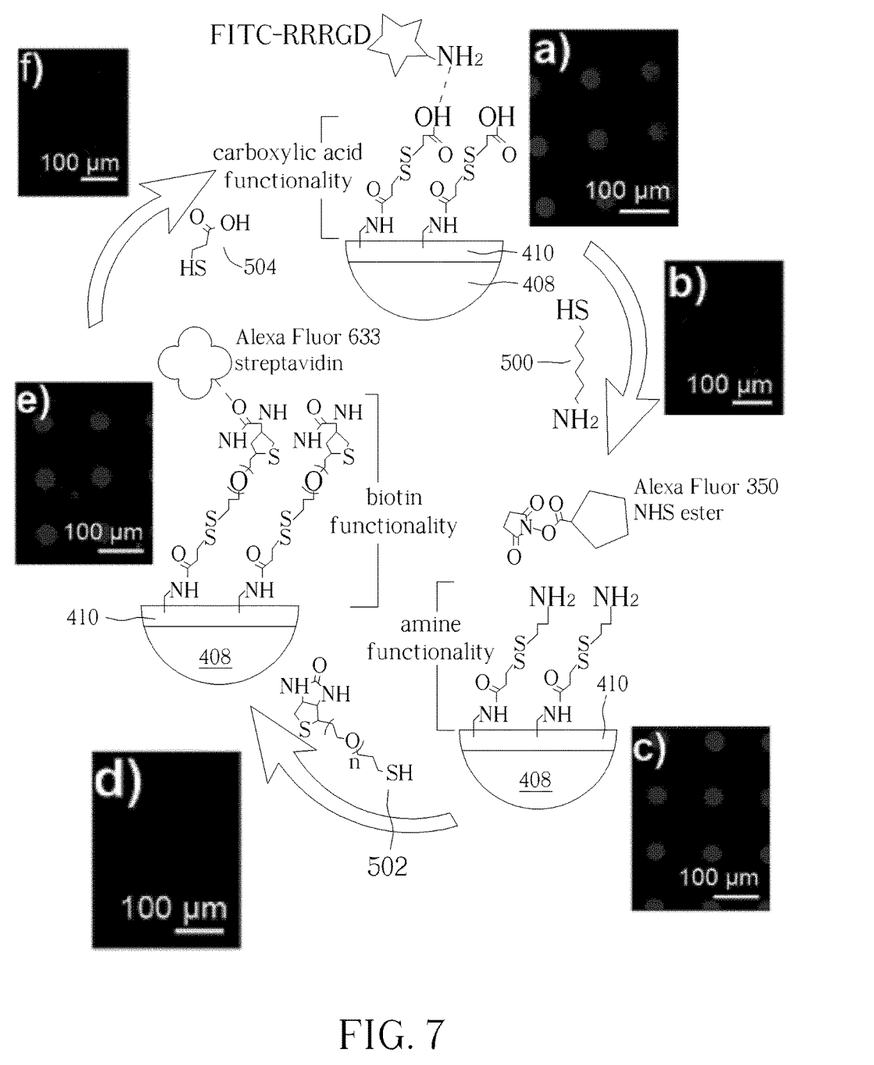
FIG. 7 shows a schematic diagram of the switching between altered surface chemical composition by using fluorescent tags.

Please refer to FIG. 7, which shows a schematic diagram of the switching between altered surface chemical composition by using fluorescent tags, wherein (a) connects the FITC-RRRGD sequence, (c) connects Alexa Fluor 350 NHS ester, (e) connects Alexa Fluor 633 peptide, (b), (d), (f) shows absence of connecting fluorescence signals. As shown in FIG. 7, The surface function was first activated with carboxyl groups by the as-deposited coating of Parylene S—S, and fluorescein (FITC)-conjugated Arg-Arg-Arg-Gly-Asp (RRRGD)(SEQ ID NO:1) peptide was used to verify the availability of the carboxyl groups by forming amide bonds between the primary amines and the activated carboxyl groups through EDC-mediated conjugation. The immobilization was performed with the aid of a μCP process that was used to bring the reactive sites between the substrate and the PDMS stamp in conformal contact to confine the reaction locations. The μCP process additionally served as a visual guide. As indicated in FIG. 7 (a), the high-contrast fluorescein signal (green 50 μm diameter circle arrays) was detected in areas where FITC-RRRGD was printed using μCP. Displacement of the immobilized FITC-RRRGD with a second functional molecule was subsequently performed by introducing 6-amine-1-hexanethiol via the thiol-disulfide interchange reaction, and the expected absence of the fluorescein signal was verified on the resulting displaced surface.

Next, a first thiol molecule 500 is applied to the target surface. In one embodiment, the first thiol molecule 500 is 6-amine-1-hexanethiol. The attachment of 6-amine-1-hexanethiol was confirmed by reacting the surface with Alexa Fluor 350 NHS ester, which forms a rigid amide bond between the NHS ester moiety and the amine group. The results show high contrast fluorescence signals (Alexa Fluor 350, blue circles), as displayed in FIG. 7(c). By contrast, for the nondisplaceable NHS ester-functionalized and amine-functionalized poly-p-xylylene coatings, firmly attached FITC-RRRGD (SEQ ID NO:1) and Alexa Fluor 350 NHS ester were respectively detected. The absence of nonspecific adsorption of the fluorescent molecules was confirmed by verifying that no Alexa Fluor 350 signal was detected on the amine-functionalized poly-p-xylylene coating as well as by performing the reaction on nonreactive poly-p-xylylene. Next, a second thiol molecule 502 is applied to the target surface, such as thiol-PEG-biotin. The displacement activity was continued by repeated application of the thiol-disulfide interchange reaction and by introducing a thiol-PEG-biotin molecule to the sample surface. The successful attachment of the biotin molecules was verified by the detection of Alexa Fluor 633 streptavidin (high specific binding affinity toward biotin), as shown in FIG. 7(e). The surface composition can always be reversibly switched to its original carboxyl functionality by displacement with a reverse component 504, such as 3-mercaptopropionic acid, as shown in FIG. 7(f). It is noted that the chemical film with Parylene S—S coated surface can connect to any thiol molecule by thiol-disulfide interaction, and can be reversed by a reverse component. The thiol molecule can have different functional group and make the chemical film exhibit different bio property.

In one embodiment, the above switch can be verified by the following steps. The switching and displacing ability of the Parylene S—S coated surfaces was achieved by altering the surface chemical compositions via disulfide interchange reactions with thiol-terminated molecules. Successful performance was then verified through conjugations with corresponding fluorescence tags. The surface function was first activated with carboxyl groups by the as-deposited coating of Parylene S—S, and a micro contact printing (μCP) process was used to bring the reactive sites between the substrate and a poly(dimethylsiloxane) (PDMS) stamp in conformal contact to confine the reaction locations. Before conducting the printing, the PDMS stamps were treated with 50 W of oxygen plasma for 2 min to render the surface hydrophilic. For the immobilization of fluorescein (FITC)-conjugated Arg-Arg-Arg-Gly-Asp (RRRGD) (SEQ ID NO: 1) peptide (FITC-RRRGD) (Yao-Hong Biotechnology Inc., New Taipei City, Taiwan), a stamp with circular arrays of 50 μm diameter and a center-center spacing of 120 μm was inked with a solution containing 10 mM FITC-RRRGD and 5 mM EDC in distilled water and then printed on Parylene S—S coating for 6 h. The resulting samples were then washed with phosphate-buffered saline containing Tween 20 (PBS-Tween 20) (pH=7.4; Sigma-Aldrich) three times, once more with pure PBS (pH=7.4; Sigma-Aldrich), and finally rinsed with distilled water. Subsequently, 100 mM glutathione (GSH; Sigma-Aldrich) aqueous solution was incubated for 6 h in 25° C. with the samples to cleave the disulfide bond. PBS-Tween 20 and pure PBS were used to clean the resulting samples. The reduced samples were then imparted with amine functionality by incubating the samples in 100 mM 6-amine-1-hexanethiol (Dojindo, Kumamoto, Japan) aqueous solution in the presence of 1 mM 2,2'-dithiodipyridine (DTP; SigmaAldrich) for 6 h to complete the disulfide interchange cycle. A byproduct of pyridine-2-thione was formed during the reaction and was observed using a UV-vis spectrophotometer (Agilent Technologies, Santa Clara, Calif., USA). The resulting samples were cleaned thoroughly three times with PBS-Tween 20 and one time with pure PBS. Successful addition of the amine groups was confirmed by fluorescence detection using Alexa Fluor 350 NHS ester (Life Technologies, Grand Island, N.Y., USA) aided by μCP during the conjugation process. The same disulfide interchange reaction was carried out on the same samples to install thiol-polyethylene glycol (PEG)-biotin (MW 5000; Nanocs, New York, N.Y., USA), and an Alexa Fluor 633 streptavidin was used for the detection. Finally, the chemical composition of the surfaces was restored to carboxyl functionality using the same interchange reaction cycle to install 3- mercaptopropionic acid (Sigma-Aldrich). Control experiments were performed in parallel on poly(4-N-hydroxy-succinimide ester-p-xylylene-co-p-xylylene) (NHS ester coating), poly(4-aminomethyl-pxylylene-co-p-xylylene) (amine coating), and poly(4-N-maleimidomethyl-p-xylylene-co-p-xylylene) (maleimide coating) coated surfaces, for which FITC-RRRGD, Alexa Fluor 350 NHS ester, and Alexa Fluor 633 streptavidin were, respectively, used for the detection of the surface functionalities followed by the same redox conditions being compared to the disulfide interchange reaction to verify the covalent bonds are not subject to any cleavage. A fluorescence microscope (TE2000-U, Nikon) was used to examine the detection process. Each experiment was conducted in triplicate.

Figure 8:
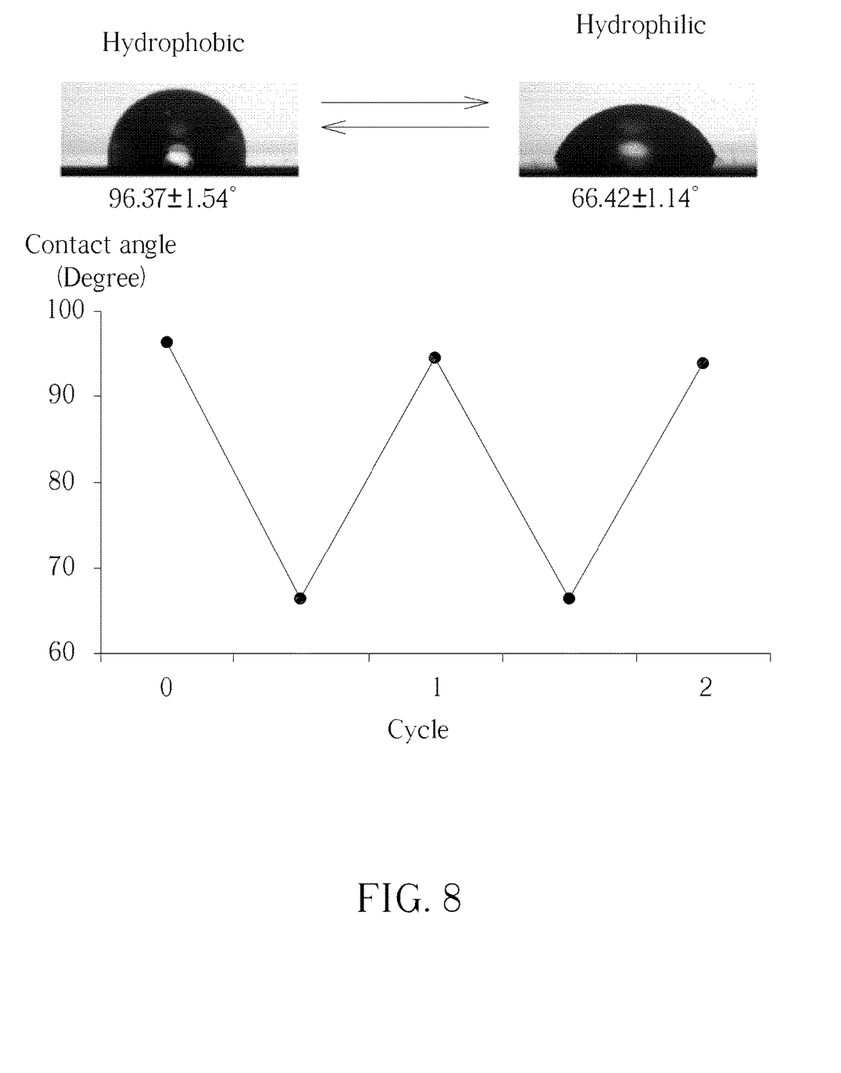
FIG. 8 shows the hydrophobicity and hydrophobicity of the surface is attributed to the attached components by the thiol-disulfide interaction.

The switched surface wettability was confirmed by measuring the water contact angle over several switch cycles. As shown in FIG. 8, which shows the hydrophobicity and hydrophobicity of the surface is attributed to the attached components by the thiol-disulfide interaction, wherein the upper figure shows the contact angle in each cycle and the lower figure shows the figures of hydrophobicity and hydrophobicity of the film. The observed rearrangements were further amplified into macroscopically detectable changes in the surface properties. Switching of the surface wettability was achieved through the interchange of a hydrophobic component such as perfluorodecanethiol and a hydrophilic component such as Cys-Lys-Asp-Lys-Asp-Asp (CKDKDD). Contact angles (CA) were measured for three subsequent switch cycles and revealed demonstrated reversibility between the hydrophobic (ca. 95° CA) and hydrophilic (ca. 66° CA) states, as shown in FIG. 8. The hydrophobicity and hydrophobicity are controlled by the surface chemical compositions of the assembled molecules of perfluorodecanethiol and CKDKDD, respectively. Scanning force microscopy did not reveal notable differences in surface roughness between systems configured with the two molecules, nor during the disulfide interchange processes, which reflects the behavior of a smooth surface for the studied systems. In one embodiment, switched surface wettability experiments were performed on Parylene S —S coated silicon wafers using the aforementioned disulfide interchange reaction cycle to immobilize a hydrophobic molecule, 1H,1H,2H,2H-perfluorodecanethiol (50 mM; Sigma-Aldrich), and a hydrophilic peptide, Cys-Lys-Asp-Lys-Asp-Asp (CKDKDD) (SEQ ID NO: 2) peptide (50 mM, Yao-Hong Biotechnology). A thorough wash process using deionized water was employed to clean the surface during each cleavage/immobilization step. The static water contact angle measurement on the resulting surfaces was performed at room temperature using a contact angle goniometer (First Ten Angstroms, Portsmouth, Va., USA) by placing 5 μL of distilled water on the surfaces. Each measurement was conducted in three different locations on the same sample and repeated for different samples in triplicate.

Figure 9:
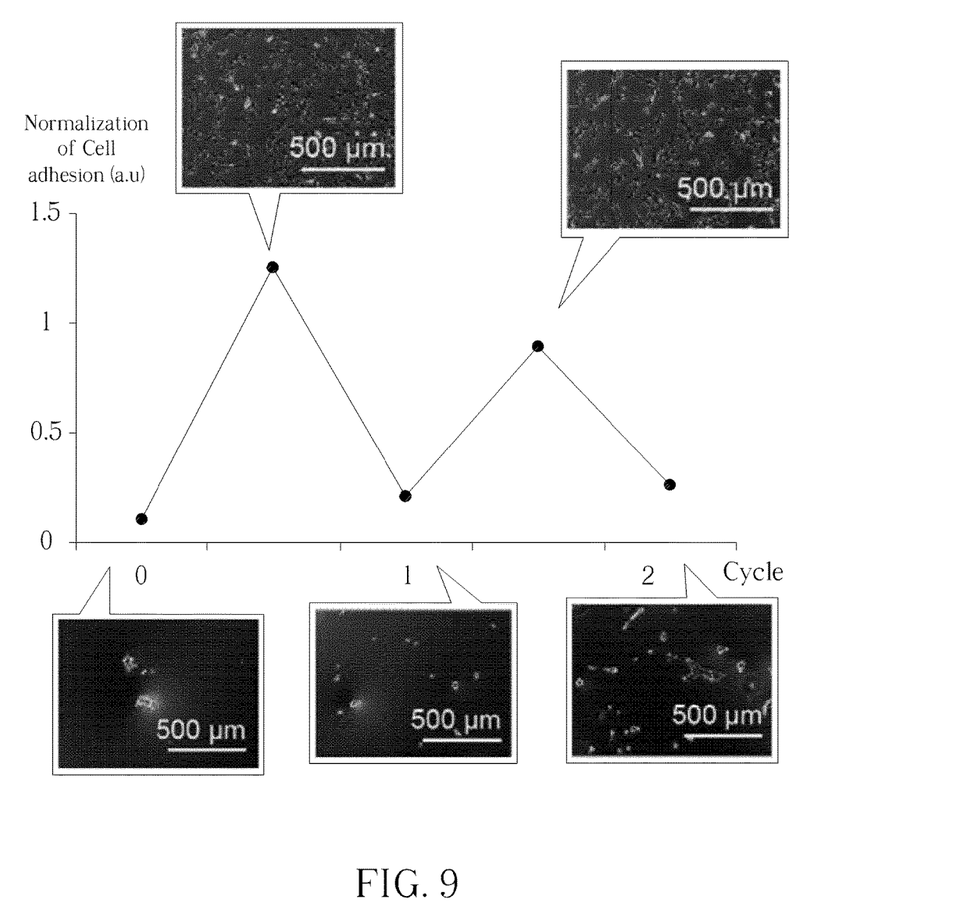
FIG. 9 shows the examination of dynamically controlled cell adhesion on a material surface over several switch cycles.

Besides the wettability, the attached bio molecules can also affect the adhesion of cells. Finally, switchability of a more complex biointerface property, cell attachment on a material surface, was demonstrated. Programmed switching was carried out between a cell-adherent state and a cell-repellent state via the immobilization and interchange of two selected biomolecules: a thiol-terminated PEG (thiol-PEG) and a RGDYCC (SEQ ID NO: 3) peptide. The growth of 3T3 fibroblast cells cultured for 24 h on thePEG-tethered Parylene S—S coated surface was found to be suppressed, which was expected due to the well-known property of the PEG motif as a repellent against cell adhesion. Please refer to FIG. 9, which shows the examination of dynamically controlled cell adhesion on a material surface over several switch cycles. As shown in FIG. 9, the resulting surfaces were subsequently displaced by the interchange reaction to attach the thiol-rich RGDYCC peptide. The surface property was correspondingly converted to a cell adherent state, as activated by RGD-mediated integrin interactions. The two types of cell adhesion properties were alternated and confirmed for three subsequent switch cycles. An intuitive control experiment was conducted in parallel by culturing 3T3 fibroblast on an amine-PEG-modified surface, where the modification was performed by immobilizing amine PEG on a nondisplaceable coating of NHS ester-functionalized poly-p-xylylene. To further characterize the switchable cell adhesion, the number of cells on the surfaces was analyzed and shown to be consistent with obtained microscope images corresponding to each cycle of the cell growth pattern. A plot of the normalized cell numbers versus switch cycle, shown in FIG. 9, unambiguously confirms the switching of dynamically manipulated cell adhesion. The previous experiment can be conducted by the following steps: Tissue culture polystyrene (TCPS) microplates (BD Falcon, Becton, Dickinson and Co., Franklin Lakes, N.J., USA) were coated with Parylene S—S, and the cell-repellent states were first prepared on the Parylene S—S coated TCPS by reacting them with an aqueous solution containing 400 mg/mL O-(2-aminoethyl)poly-(ethylene glycol) (amino-PEG; MW 5000; Sigma-Aldrich), with the addition of 5 mM EDC during the reaction. The cell-repellent surface modification during the disulfide interchange reaction was performed by reacting the plates with thiol-terminated PEG (400 mg/mL, MW5000; Sigma-Aldrich). These reactions were maintained at 25° C. for 6 h. For the case of the cell-adherent surface modification, the Parylene S—S coated TCPS substrates were reacted with a 10 mM Arg-Gly-Asp-Tyr-Tyr-Cys (RGDYYC; Yao-Hong Biotechnology) aqueous solution at 25° C. for 6 h. The switchability between the cell-repellent surface and the cell-adherent surface was studied by first culturing cells onto the PEG-modified surfaces (Parylene S—S coated TCPS plates) with a seeding density of $6 \times 10^4$ cells/well. Two cell lines including commercially obtained 3T3 fibroblast cells (clone A31, CCL-163; ATCC, Manassas, Va., USA) and adipose-derived stem cells (ASCs) isolated from porcine adipose tissues (performed following institutional guidelines30 and were provided by Prof. Shih-Torng Ding, Department of Animal Science and Technology, National Taiwan University, Taiwan) were used in the study. The cells were grown in Dulbecco's modified Eagle's medium (DMEM; HyClone, Logan, Utah, USA) containing 10% fetal bovine serum (Biological Industries, Kibbutz Beit-Haemek, Israel) and 1% penicillin-streptomycin amphotericin B solution (catalog no. 03-033-1B; Biological Industries) at 37° C. in a humidified atmosphere containing 5% $CO_2$ and 95% air for 24 h. The switching between the cell-repellent and cell-adherent states was initiated using the aforementioned disulfide interchange reaction cycle to cleave/immobilize thiol-terminated PEG. The cells were then washed once with PBS (0.15 M, pH 7.4), detached by incubation with 0.5% trypsin/0.2% EDTA (Biological Industries), and re-suspended with fresh culture medium. The resulting samples were then subjected to the disulfide interchange reaction to install RGDYCC, and subsequently new 3T3 cells, with the same seeding density ($6 \times 104$ cells/well) and the same culture conditions, were cultured on the RGDYCC-modified plates. Four replicates per tested surface and three independent experiments were performed. A control experiment was performed in parallel using an NETS-ester coating to modify the TCPS plates with the same cell seeding density and culturing conditions. For cell counting, the cell suspensions were diluted in a 1:1 ratio with a 0.4% Trypan Blue solution (SigmaAldrich). The cell number and viability were determined by dye exclusion of live cells on a hemocytometer. The cell adhesion ratio was determined by dividing the number of cells on PEG- and/or RGDimmobilized surfaces with the number of cells on TCPS control surfaces. An inverted microscope (Olympus, Tokyo, Japan) was used to visualize the cell growth pattern for each step during the disulfide interchange cycle.

In summary, a new concept in poly-p-xylylene chemistry has been realized, mimicking the displaceable and dynamically controlled properties of real biological systems and able to fulfill the essential need for a tailored biointerface. The key features of this advanced version of poly-p-xylylene include the following: (i) There is a reversible mechanism for attaching/detaching biomolecules. For example, installed growth factor proteins are cleaved when deactivation is required. Additionally, timed control of eluting drugs or bio functional molecules from the material surfaces to enable the delivery of these molecules to the target sites is also possible. (ii) There is a mechanism of restoring biological functions with repeated cycles or a programmed displacement of new functions.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of forming a chemical film comprising:
   providing a substrate;
   performing a chemical vapor deposition (CVD) process to form a chemical film on the substrate, wherein the chemical film comprises poly-p-xylylene with disulfide functional group, wherein monomer of the poly-p-xylylene is formed by adding 3,3'-dithiodipropionic acid and N-ethyl-N'-(3-(dimethylamino)propyl)carbodiimide into 4-aminomethyl [2,2] paracyclophane, thereby obtaining a paracyclophane comprising a disulfide functional group.

2. The method of forming a chemical film according to claim 1, wherein the chemical vapor deposition process is conducted at a temperature of 500 to 800° C.

3. The method of forming a chemical film according to claim 1, further comprising:
   performing a first thiol-disulfide interaction to make a first thiol molecule connect to the chemical film.

4. The method of forming a chemical film according to claim 3, further comprising:
   after the first thiol-disulfide interaction, performing a second thiol-disulfide interaction to replace the first thiol molecule by a second thiol molecule.

5. The method of forming a chemical film according to claim 4, wherein the first thiol molecule is different from the second thiol molecule.

* * * * *